(12) United States Patent
Gregg

(10) Patent No.: US 6,569,046 B1
(45) Date of Patent: May 27, 2003

(54) BELT WEAR DETECTION SYSTEM AND METHOD

(75) Inventor: Michael John William Gregg, Lincoln, NE (US)

(73) Assignee: The Goodyear Tire & Rubber Company, Akron, OH (US)

( * ) Notice: Subject to any disclaimer, the term of this patent is extended or adjusted under 35 U.S.C. 154(b) by 0 days.

(21) Appl. No.: 09/786,798

(22) PCT Filed: Oct. 23, 1998

(86) PCT No.: PCT/US98/22573

§ 371 (c)(1),
(2), (4) Date: Mar. 7, 2001

(87) PCT Pub. No.: WO00/25040

PCT Pub. Date: May 4, 2000

(51) Int. Cl.[7] .................................................. F16H 7/22
(52) U.S. Cl. ........................ 474/106; 474/103; 474/102
(58) Field of Search .................................. 474/106, 103, 474/102, 107, 191; 250/559.02, 559.36; 198/807; 356/429, 614, 373; 355/208, 212; 399/395, 303, 313

(56) References Cited

U.S. PATENT DOCUMENTS

| | | | | |
|---|---|---|---|---|
| 3,543,597 A | * | 12/1970 | De Schamphelaere et al. | .. 474/103 |
| 4,626,230 A | | 12/1986 | Yasuhara | ..................... 474/106 |
| 4,627,702 A | * | 12/1986 | Anderson | ..................... 474/191 |
| 4,959,040 A | | 9/1990 | Gardner et al. | ............... 474/103 |
| 5,515,139 A | * | 5/1996 | Hou et al. | ..................... 198/807 |
| 5,519,230 A | * | 5/1996 | Hubble et al. | .......... 250/559.02 |
| 5,565,965 A | * | 10/1996 | Costanza et al. | ....... 250/559.36 |
| 5,964,339 A | * | 10/1999 | Matsuura et al. | ........... 198/807 |
| 6,141,525 A | * | 10/2000 | Tahara | ......................... 399/303 |
| 6,260,880 B1 | * | 7/2001 | Hada et al. | ................... 180/268 |
| 6,377,347 B1 | * | 4/2002 | Tuck et al. | ................... 356/429 |

FOREIGN PATENT DOCUMENTS

| | | | |
|---|---|---|---|
| DE | 3844358 A1 | * 7/1990 | ........... B24B/21/20 |
| DK | 3334612 | 4/1985 | |
| EP | 0571887 | 12/1993 | |
| EP | 0698752 | 2/1996 | |

* cited by examiner

*Primary Examiner*—Marcus Charles
(74) *Attorney, Agent, or Firm*—Nancy T. Krawczyk

(57) ABSTRACT

A system and method for detecting wear and the beginning of the mechanism of belt failure. A sensor (5) detects when a self tracking drive belt (1) tracks off center due to the asymmetrical wear (3) of the belt (1). The sensor (5) may be a simple mechanical or optical switch which is activated upon contact or a complex system which can detect the relative movement of the belt (1) when the belt (1) tracks to either side of the pulley (4). An audible or electrical signal indicates that the belt (1) needs to be changed.

6 Claims, 1 Drawing Sheet

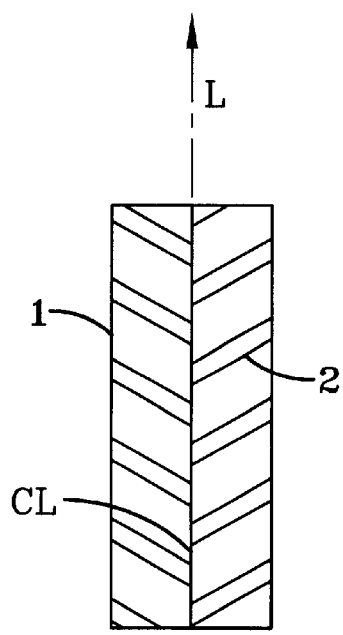
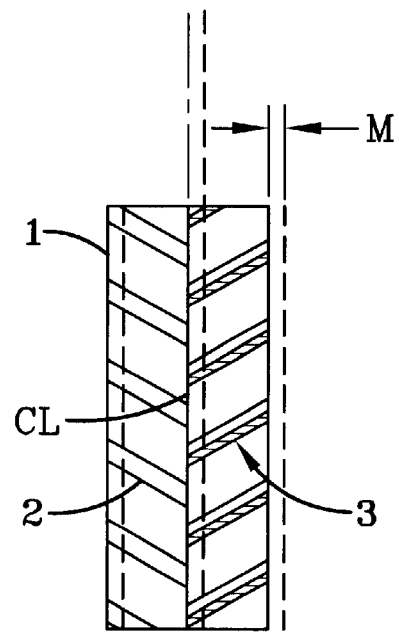
FIG-1    FIG-2
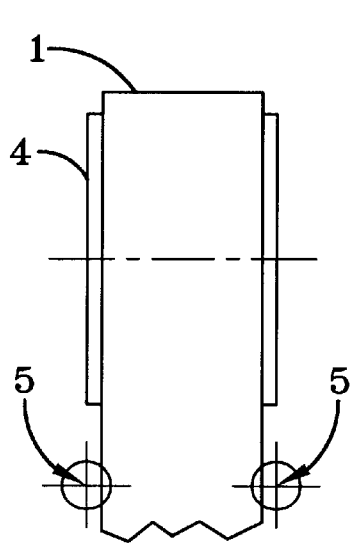
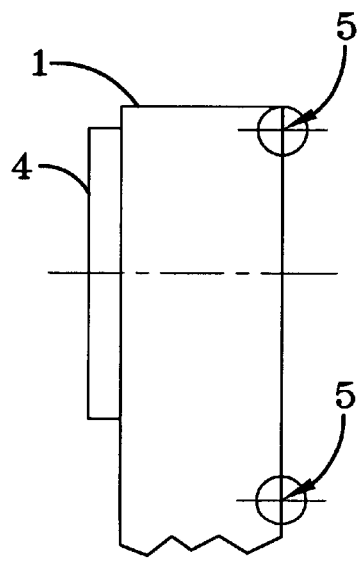
FIG-3    FIG-4

BELT WEAR DETECTION SYSTEM AND METHOD

TECHNICAL FIELD

The disclosed invention is related to wear detection for belts. More specifically, the disclosed method and apparatus are directed to early warning wear detection for helical offset tooth belts. The disclosed method is highly useful in determining early wear of vehicle timing belts.

BACKGROUND ART

Conventional synchronous drive belts have teeth placed at right angles to the belt mid-circumferential line. Such belts are well illustrated in U.S. Pat. Nos. 4,108,011 and 4,690,664. In these known prior art belts, the whole tooth engages with a corresponding pulley cavity at the same time. When such belts wear, the belt begins to oscillate from side to side on the pulleys. To prevent the belt oscillation from pulling the belt off of the drive system, the pulleys of the system are provided with flanges. Wear of such belts is determined by either visual inspection of cracks or breaks, or complete failure of the belt.

U.S. Pat. No. 5,209,705 discloses a synchronous drive belt with at least two transversely adjacent rows of teeth, having centerlines, uniformly spaced apart in the longitudinal direction by a pitch length and extending obliquely to the longitudinal directional. The teeth in the transversely adjacent rows are at oppositely balanced angles and the centerlines of said adjacent teeth are offset from each other by a distance of from 10% to 90% of the pitch length. Such belts are known in shorthand terminology as helical-offset-tooth (HOT) belts. Due to the tooth configuration, the HOT belt is a self tracking belt, that is, there is no normal oscillation of the belt during belt operation. The associated pulleys reflect this aspect of the belt, in that the pulleys are not provided with flanges.

Other types of known self-tracking belts are non-offset teeth belts, wherein the belt has at least two transversely adjacent rows of teeth, the teeth having centerlines extending obliquely to the longitudinal direction. These belts have teeth formed in a chevron pattern. The pulleys associated with chevron toothed belts also do not require flanges, since there is no oscillation of the belt.

The disclosed invention is directed towards the use of a warning system for synchronous belts. The warning system may also be a multiple stage warning system. The disclosed invention may be employed with any synchronous self-tracking belt, such as the HOT belt and chevron tooth belt, and has great applicability for automotive timing belts.

Currently, every vehicle engine has a timing mechanism, either a timing belt or timing chain, for operation of the engine. When the timing mechanism is worn, complete failure of the mechanism results in permanent engine damage, or at best, strands the motorist. There is no automatic detection system or method for determining wear of a timing belt, only physical inspection is possible and is not completely accurate.

U.S. Pat. No. 4,626,230 discloses a device for sensing damage to a toothed belt. However, the sensing device only detects wear of the belt due to tooth breakage, and cannot determine the wear of the belt due to the teeth being worn down during the life of the belt, which also necessitates the replacement of the belt.

Because of the extreme results at failure, one preventative measure is automatic replacement of the belt every 60,000 miles, regardless of the actual wear of the belt. The other conventional method of avoiding catastrophic failure is to use a timing chain, instead of a belt. The timing chain becomes very noisy long before failure occurs alerting the driver to the problem so the chain can be replaced. However, timing chains are heavy and the total drive system is more expensive than a belt drive system.

The present invention will result in more timely assessment of replacement for engine timing belts and less reliance on inaccurate human assessment of belt wear, as well as enable vehicle manufacturers to use the less expensive, lighter weight belt drive systems. The present invention will lead to fewer unnecessary replacements of belts.

SUMMARY OF THE INVENTION

The goal of the present invention is an improved wear detection system for use with a synchronous self-tracking belt.

A further aspect of the invention is a two stage warning system for belt wear.

A further aspect of the invention is a multiple stage belt wear detection system.

A benefit of the disclosed invention is a soft failure warning system which prevents catastrophic failure of the synchronous self-tracking drive belt.

The invention is a system employing a helical offset tooth belt and a sensor near at least one side of the belt.

The invention may also employ a sensor mounted on the opposite side of the belt.

The invention may also employ sensors mounted near the belt to provide for a two-stage or multi-stage wear detection system.

One benefit of the disclosed invention is a wear detection system for automotive timing belts.

A further benefit of the invention is a two stage warning system for automotive timing belts.

A further benefit of the invention is a multiple stage wear detection system for automotive timing belts.

BRIEF DESCRIPTION OF DRAWINGS

The invention will be described by way of example and with reference to the accompanying drawings in which:

FIG. 1 is a drawing of the toothed surface of a HOT belt;

FIG. 2 is a drawing of a worn HOT belt;

FIG. 3 is a drawing of the HOT belt mounted on a pulley in accordance with the present invention; and FIG. 4 is a drawing of a worn HOT belt mounted on a pulley in accordance with the present invention.

DETAILED DESCRIPTION OF THE PREFERRED EMBODIMENTS

As noted above, and represented in FIG. 1, a HOT belt 1 has at least two transversely adjacent rows of teeth 2 uniformly spaced apart in the longitudinal direction L and extending obliquely to the longitudinal directional L. The teeth 2 in the transversely adjacent rows are at oppositely balanced angles, relative to the centerline CL of the belt 1. In a belt drive system, the belt is mounted on at least one pulley. In the self-tracking chevron tooth belt, the teeth 2 as seen in FIG. 1 would be of a chevron configuration, that is, the teeth 2 in the adjacent rows would not be offset from one another. The following discussion is directed specifically toward the illustrated HOT belt 1, but is equally applicable to the self-tracking chevron belt.

It has been determined that when the self-tracking belt 1 wears, the wear is not symmetrical for adjacent rows of teeth 2, see FIG. 2. That is, the teeth 2 on one side of the belt centerline CL present a greater wear 3 than the teeth 2 on the opposing side of the centerline CL. Because the belt 1 is self-tracking, due to the tooth 2 and corresponding pulley configuration (see U.S. Pat. No. 5,209,705), as one set of teeth wears, the belt 1 tracks off center, resulting in a permanent misalignment M of the belt 1 on a pulley, as opposed to the oscillation of conventional straight-toothed belts. The misalignment M is directly proportional to the amount of wear 3 of the belt 1.

The misalignment M of the belt 1 is used advantageously to provide for a wear indicating system for the belt 1. The system is illustrated, in a highly simplified manner, in FIG. 3. The belt 1 is mounted on the pulley 4, with the belt teeth 2 engaging the pulley 4. A sensor 5 is mounted in alignment with the edges of the belt 1 or pulley 4. The sensor 5 may be any type of conventional sensor, from a simple optical or mechanical device which is triggered upon contact or interruption to a more complex system employing lasers which can detect both the relative displacement of the belt in directions both towards and away from the sensor. The primary requirement of the sensor 5 is that it is activated when the belt 1 when the sensor detects an increase or decrease in spacing between the belt edge and the sensor 5. The sensor sends either an electrical or audible signal that the belt 1 needs to be changed. FIG. 3 illustrates a sensor 5 mounted on each pulley side.

The system may employ a single sensor may be mounted on one side, or a plurality of sensors only mounted on one side for the multiple stage warning system discussed below. One sided mounting of the sensors may be employed when using the laser system described previously. Additionally, if it is known which side of the pulley the belt tracks to upon wear, a single sensor may be mounted on that side of the pulley. To achieve a known tracking pattern, one side of the belt, relative to the centerline, is formed with a greater width than the opposing belt helf.

FIG. 4 illustrates the system in operation, illustrating only one activated sensor. As the belt 1 is worn, and one side of the belt 1 exhibits greater wear 3 than the other side, the belt 1 begins to travel predominately along one side of the pulley 1 more than the other side, generating the misalignment M. As the belt 1 begins traveling on one side of the pulley 4, the sensor 5 is activated. The sensor 5 sends an electrical or audible signal indicating a misalignment. The electrical signal is sent to a warning system for informing the operator of the timing belt wear. The use of an electrical signal is applicable if the sensor is used in connection with automotive timing belts.

FIGS. 3 and 4 illustrate a very simplified one-stage warning system. The illustrated warning system may be expanded into a multi-stage warning system by the placement on/or near the pulley 4 or belt 1 of more sensors 5 axially inward of the illustrated sensors 5. If two more sensors 5 are employed, a two stage warning system is created. The first and axially inward sensor may trigger a warning of initial wear, while activation of the axially outer sensor may trigger a warning of advanced wear or imminent failure of the belt. If the belt 1 used is of a relatively large size, i.e. width and tooth depth, multiple sensors 5 may be used to indicate increased levels of wear 3, resulting in a multiple-stage warning system.

Use of the inventive wear detection system with an automotive timing HOT belt, or chevron toothed belt, may be employed in the following manner. When a first sensor is activated, a warning light on the vehicle dashboard goes on. When a second sensor is activated, the engine may be shifted into "limp" mode, forcing the operator to have the engine inspected and the timing belt replaced, or a buzzer may go off in combination with the vehicle dashboard light, also forcing the operator to have the vehicle inspected.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described which will be within the full intended scope of the invention as defined by the following appended claims.

What is claimed is:

1. A system for detecting wear in a self-tracking toothed belt (1) when being driven by a mating pulley (4), the system comprising a self-tracking toothed belt (1) mounted on and being driven by at least one mating pulley (4), and at least one sensor (5) mounted in alignment with the belt (1), the system being characterized by:

the at least one sensor (5) being activated when there is an axial displacement of the belt (1) upon the mating pulley (4) as the result of belt wear (3).

2. A system as set forth in claim 1 wherein the system is further characterized by the at least one sensor (5) being mounted in alignment with each side of the belt (1).

3. A system as set forth in claim 1 wherein the system is further characterized by at least two of the at least one sensors (5) mounted in alignment along at least one side of the belt (1).

4. A method for detecting wear in a self-tracking toothed belt (1) when being driven by a mating pulley (4), the method comprising mounting and driving a self-tracking toothed belt (1) on at least one mating pulley (4), and mounting at least one sensor (5) in alignment with the belt (1), the system being characterized by:

activating the at least one sensor (5) when there is an axial displacement of the belt (1) upon the mating pulley (4) as a result of belt wear (3).

5. A method as set forth in claim 4 wherein the method is further characterized by mounting the at least one sensor (5) in alignment with each side of the belt (1).

6. A method as set forth in claim 4 wherein the method is further characterized by mounting at least two of the at least one sensors (5) in alignment along at least one side of the belt (1).

* * * * *